(12) United States Patent
Katz et al.

(10) Patent No.: US 6,277,827 B1
(45) Date of Patent: Aug. 21, 2001

(54) SINGLE MORPHIC FORMS OF METALLOPROTEINASE INHIBITORS

(75) Inventors: Ruth Bernice Katz; Graham Robert Evans, both of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/425,572

(22) Filed: Oct. 22, 1999

(30) Foreign Application Priority Data

Oct. 23, 1998 (GB) .................................................. 9823335
Oct. 23, 1998 (GB) .................................................. 9823336

(51) Int. Cl.$^7$ ........................ A61K 38/05; C07D 207/24; C07D 233/72
(52) U.S. Cl. ........................ 514/19; 548/319.5; 548/546; 424/451; 424/464
(58) Field of Search ................................ 548/319.5, 546; 514/19; 424/451, 464

(56) References Cited

FOREIGN PATENT DOCUMENTS

| 96/11209 | 4/1996 | (WO) . |
| 97/12902 | 4/1997 | (WO) . |
| 98/39024 | 9/1998 | (WO) . |

*Primary Examiner*—Fiona T. Powers
(74) *Attorney, Agent, or Firm*—Saliwanchik, Lloyd & Saliwanchik

(57) ABSTRACT

A single morphic form of a compound selected from 2S-[4-(2,5-dioxopyrrolidin-1-yl)-2S-mercaptobutyrylamino]-4-methylpentanoic acid (2,2-dimethyl-1S-methylcarbamoylpropyl)amide and 2S-[2S-mercapto-4-(3,4,4-trimethyl-2,5-dioxoimidazolidin-1-yl)butyrylamino]-4-methylpentanoic acid (2,2-dimethyl-1S-methylcarbamoylpropyl)amide, isolable as such.

20 Claims, 2 Drawing Sheets

SINGLE MORPHIC FORMS OF METALLOPROTEINASE INHIBITORS

FIELD OF THE INVENTION

This invention relates to new crystalline forms of known compounds, having therapeutic utility, that are metalloproteinase inhibitors.

BACKGROUND OF THE INVENTION

As potential therapeutic agents, in the treatment of inflammatory and other conditions, there is considerable interest in compounds that have the ability to inhibit matrix metalloproteinases and also the release of tumour necrosis factor. Two known compounds of this type are 2S-[4-(2, 5-dioxopyrrolidin-1-yl)-2S-mercaptobutyrylamino]-4-methylpentanoic acid (2,2-dimethyl-1S-methylcarbamoylpropyl)amide (herein Compound A) and 2S-[2S-mercapto-4-(3,4,4-trimethyl-2, 5-dioxoimidazolidin-1-yl)butyrylamino]-4-methylpentanoic acid (2,2-dimethyl-1S-methylcarbamoylpropyl)amide (herein Compound B). Compound A is disclosed in WO-A-96/11209 and WO-A-98/39024. Compound B is disclosed in WO-A-97/12902 (generically) and WO-A-98/39024 (specifically).

SUMMARY OF THE INVENTION

This invention is based on the surprising discovery that Compounds A and B exists in more than one morphic form. Further, it has been found that, by comparison with the products whose preparation has previously been reported, novel compounds can be isolated as a single morphic form (this term is used herein to describe a crystalline form having a single morphology).

A novel morphic form according to the present invention is reproducibly isolable as a single crystalline species. It may be characterised by its crystalline structure, its X-ray powder diffraction (XRPD) pattern, its DSC thermogram, and/or by a different melting point from that previously reported. It may be essentially free of bound solvent, non-hygroscopic, and more thermodynamically stable, i.e. both more chemically and physically stable than the compound as previously reported. This stability makes the novel species particularly suitable for formulation into pharmaceutical formulations, following milling and, if appropriate, compression. It may also provide improved bioavailability.

DESCRIPTION OF THE DRAWINGS

The accompanying drawings are XRPD traces obtained for Compounds A and B, respectively.

DESCRIPTION OF THE INVENTION

The present invention depends in part on the solvent chosen for the crystallisation. Suitable procedures are shown in the Examples, below. Other procedures have produced other morphic forms ofthe same compounds, but these generally have properties that are unsuitable for the purposes of the present invention, e.g. not being isolable as a single morphic form.

One criterion for choosing the desired product is by observation of a single sharp peak in the DSC thermogram. Another may be a high melting point, depending on the desire for increased solubility or stability.

As indicated above, compounds of the invention have a morphic or crystalline form that is unchanged on milling. They are therefore particularly suitable for use in solid, discrete pharmaceutical unit dosage forms such as filled capsules, etc. Further, they are unchanged under compression used in a tableting process.

For the purposes of formulation, a compound of the invention is mixed with a pharmaceutically acceptable carrier. Examples of suitable carriers and also suitable doses can readily be determined by one skilled in the art or are known; see also the PCT publications identified above, the contents of which are incorporated herein by reference.

The following Examples illustrate how single morphic forms according to the present invention may be prepared.

EXAMPLE 1

Compound A is dissolved with heating to 50° C. in 1.5 volumes of isopropyl acetate under an atmosphere of nitrogen. To this solution is added 0.56 volumes of heptane, and the mixture is slowly cooled to 10° C. The solid is isolated by filtration, washed with 1:1 isopropyl acetate/heptane, and dried in vacuo at approximately 65° C.

Figure 1:
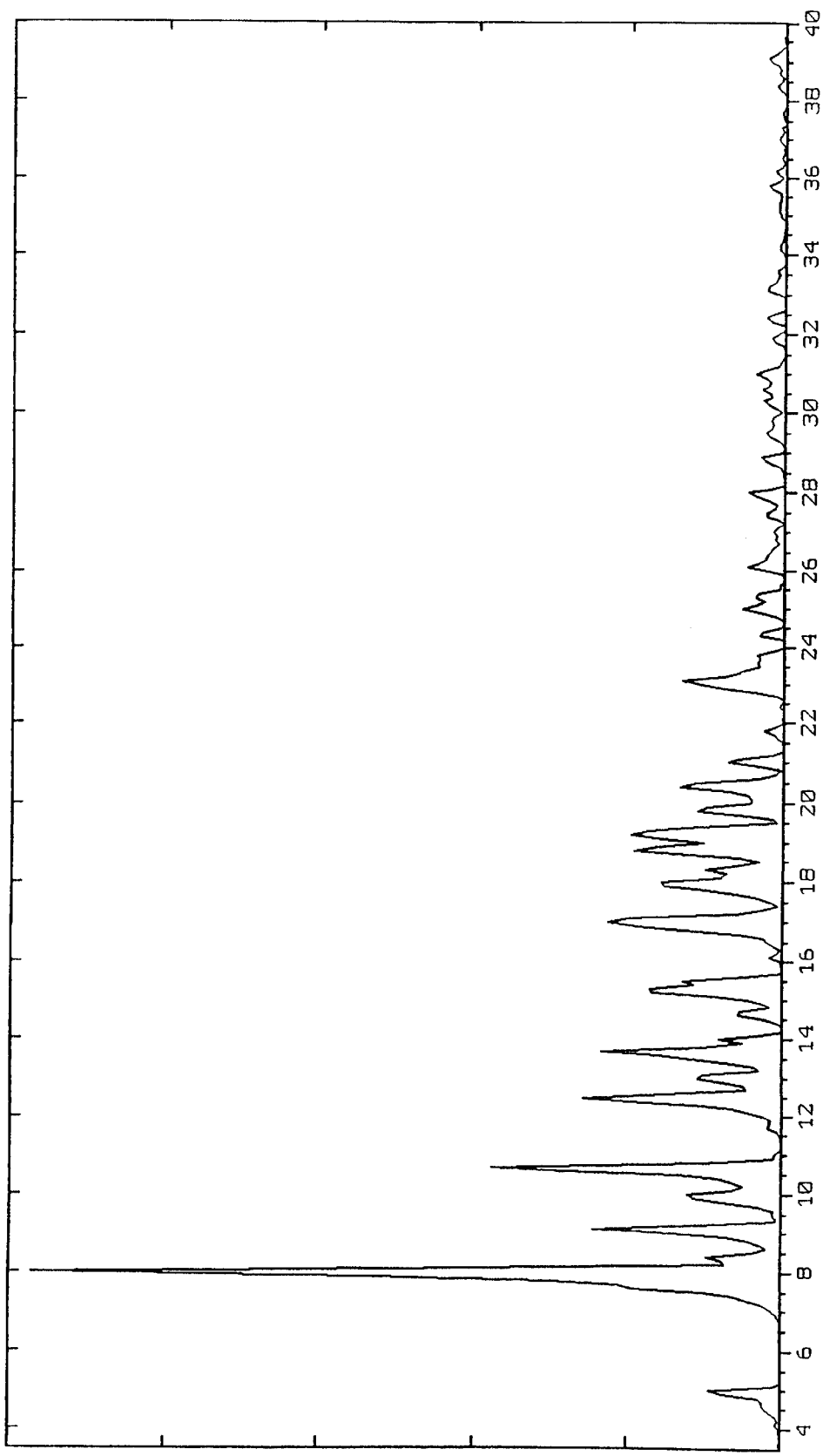

The melting point of the product is 148° C. The XRPD trace is shown in FIG. 1. The major peaks are at 8.0, 9.1, 10.7, 12.4, 13.6 and 17.0.

EXAMPLE 2

Compound B is dissolved with heating in 3 volumes of isopropyl acetate under an atmosphere of nitrogen, and the water content assessed by Karl Fischer titration to be less than approximately 0.5%. The solution is heated to reflux with stirring and 2.5 volumes of heptane is added slowly. Crystallisation is initiated by the addition of seed crystals at 80–85° C. The suspension is allowed to cool to ambient temperature and the solid isolated by filtration. The filter cake is washed with a mixture of isopropyl acetate (1.6 volumes) and heptane (1.25 volumes) and dried in vacuo at approximately 50° C.

Figure 2:
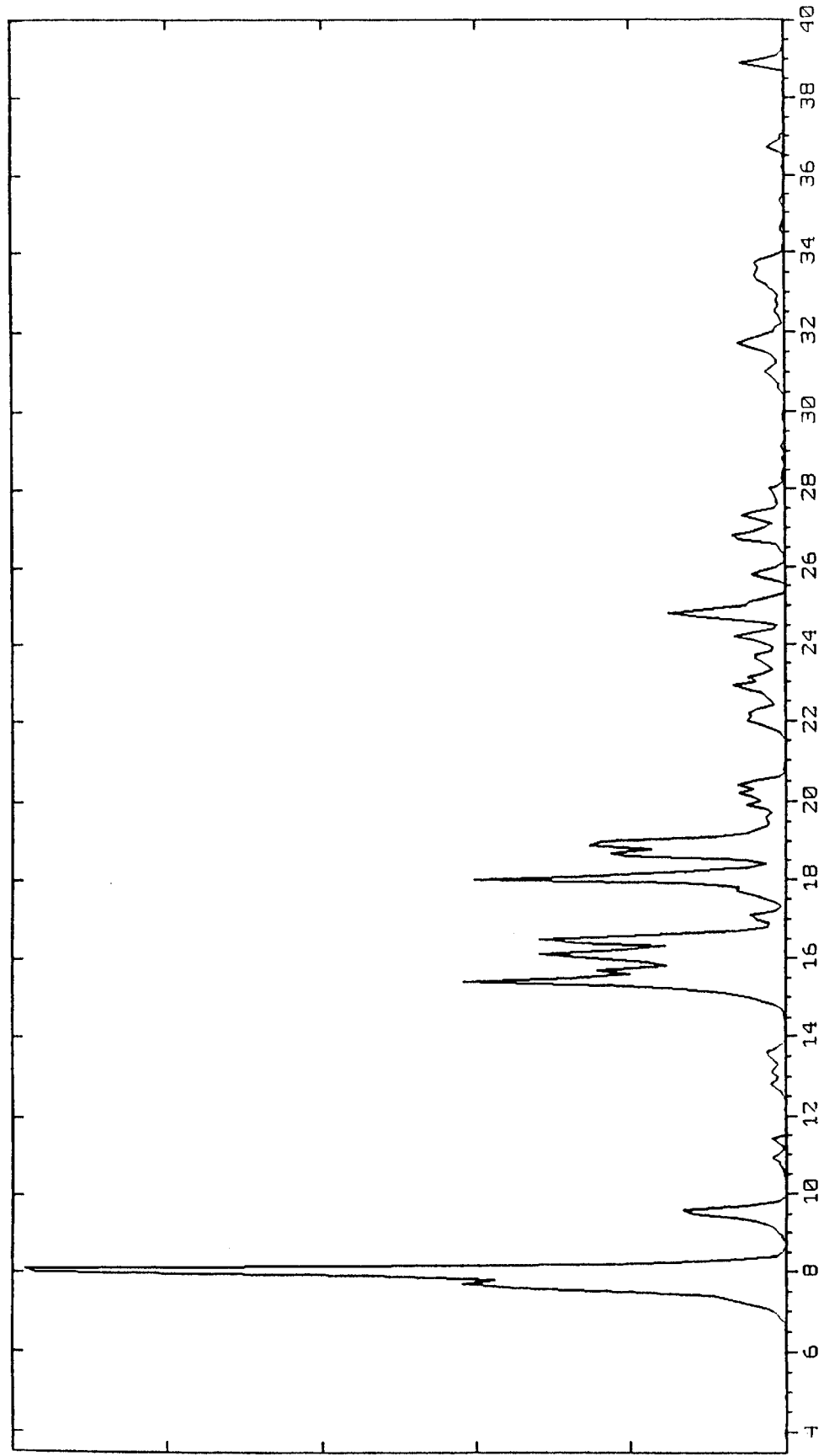

The melting point of the product is 164° C. The XRPD trace is shown in FIG. 2. The major peaks are at 7.6, 8.0, 15.3, 16.1, 16.5 and 17.8.

What is claimed is:

1. A single morphic form of a compound of 2S-[4-(2, 5-dioxopyrrolidin-1-yl)-2S-mercaptobutyrylamino]-4-methylpentanoic acid (2,2-dimethyl-1S-methylcarbamoylpropyl)amide, said compound having X-ray powder diffraction peaks at 8.0, 9.1, 10.7, 12.4, 13.6 and 17.0, isolable as such.

2. The single morphic form according to claim 1, which is non-hygroscopic.

3. The single morphic form according to claim 2, which is solvent free.

4. The single morphic form according to claim 1, which is solvent-free.

5. A pharmaceutical unit dosage form comprising a single morphic form according to claim 1, obtainable by milling, and a pharmaceutically-acceptable carrier.

6. The dosage form according to claim 5, which is a filled capsule.

7. The dosage form according to claim 5, which is a compressed tablet.

8. A method for the manufacture of a dosage form according to claim 5, which comprises milling the morphic form, mixing it with the carrier, and optionally also compressing the mixture, wherein the structure of the morphic form is unchanged by the method.

9. The method for the manufacture of a dosage form according to claim 8, wherein the dosage form is a filled capsule.

10. The method for the manufacture of a dosage form according to claim 8, wherein the dosage form is a compressed tablet.

11. A single morphic form of a compound of 2S-[2S-mercapto-4-(3,4, 4-trimethyl-2,5-dioxoimidazolidin-1-yl) butyrylamino]-4-methylpentanoic acid (2,2-dimethyl-1S-methylcarbamoylpropyl) amide, said compound having X-ray powder diffraction peaks at 7.6, 8.0, 15.3, 16.1, 16.5 and 17.8, isolable as such.

12. The single morphic form according to claim 11, which is non-hygroscopic.

13. The single morphic form according to claim 12, which is solvent free.

14. The single morphic form according to claim 11, which is solvent-free.

15. A pharmaceutical unit dosage form comprising a single morphic form according to claim 11, obtainable by milling, and a pharmaceutically-acceptable carrier.

16. The dosage form according to claim 15, wich is a filled capsule.

17. The dosage form according to claim 15, which is a compressed tablet.

18. A method for the manufacture of a dosage form according to claim 15, which comprises milling the morphic form, mixing it with the carrier, and optionally also compressing the mixture, wherein the structure of the morphic form is unchanged by the method.

19. The method for the manufacture of a dosage form according to claim 18, wherein the dosage form is a filled capsule.

20. The method for the manufacture of a dosage form according to claim 18, wherein the dosage form is a compressed tablet.

* * * * *

UNITED STATES PATENT AND TRADEMARK OFFICE
CERTIFICATE OF CORRECTION

PATENT NO. : 6,277,827 B1　　　　　　　　　　　　　　　　　Page 1 of 1
DATED : August 21, 2001
INVENTOR(S) : Ruth Katz, Graham Robert Evans It is certified that error appears in the above-identified patent and that said Letters Patent is hereby corrected as shown below:

Column 3,
Line 5, "(3,4, 4-trimethyl-2,5-dioxoimidazolidin-1-yl)" should read -- (3,4,4-trimethyl-2,5-dioxoimidazolidin-1-yl) --.

Column 4,
Line 1, "wich" should read -- which --.

Signed and Sealed this

Twelfth Day of March, 2002

Attest:

JAMES E. ROGAN
*Attesting Officer*　　　*Director of the United States Patent and Trademark Office*